United States Patent
Wang et al.

(10) Patent No.: US 12,173,338 B2
(45) Date of Patent: Dec. 24, 2024

(54) GENETICALLY ENGINEERED BACTERIA, ITS CONSTRUCTION METHOD AND ITS APPLICATION IN PRODUCING NAD$^+$ METHOD

(71) Applicant: HEFEI KNATURE BIO-PHARM CO., LTD., Anhui (CN)

(72) Inventors: Wei Wang, Anhui (CN); Kanglin Wang, Anhui (CN); Minjie Fu, Anhui (CN); Yonghong Jin, Anhui (CN); Feng Tian, Anhui (CN); Heping Jia, Anhui (CN); Zhihao Hu, Anhui (CN)

(73) Assignee: HEFEI KNATURE BIO-PHARM CO., LTD., Anhui (CN)

( * ) Notice: Subject to any disclaimer, the term of this patent is extended or adjusted under 35 U.S.C. 154(b) by 657 days.

(21) Appl. No.: 17/256,364

(22) PCT Filed: Jun. 11, 2020

(86) PCT No.: PCT/CN2020/095553
§ 371 (c)(1),
(2) Date: Dec. 28, 2020

(87) PCT Pub. No.: WO2021/120548
PCT Pub. Date: Jun. 24, 2021

(65) Prior Publication Data
US 2021/0371843 A1    Dec. 2, 2021

(30) Foreign Application Priority Data

Dec. 20, 2019 (CN) .......................... 201911326087.0

(51) Int. Cl.
| | | |
|---|---|---|
| *C12N 9/78* | (2006.01) | |
| *C12N 9/00* | (2006.01) | |
| *C12N 9/10* | (2006.01) | |
| *C12N 9/12* | (2006.01) | |
| *C12P 19/36* | (2006.01) | |

(52) U.S. Cl.
CPC ............ *C12N 9/78* (2013.01); *C12N 9/1077* (2013.01); *C12N 9/1241* (2013.01); *C12N 9/93* (2013.01); *C12P 19/36* (2013.01); *C12Y 204/02012* (2013.01); *C12Y 207/07001* (2013.01); *C12Y 305/01019* (2013.01); *C12Y 603/05001* (2013.01)

(58) Field of Classification Search
None
See application file for complete search history.

(56) References Cited

U.S. PATENT DOCUMENTS

2009/0246803 A1* 10/2009 Imai ................. C12P 19/36
435/7.8
2020/0224227 A1*  7/2020 Lee .................. C12P 13/001

FOREIGN PATENT DOCUMENTS

| CN | 1270631 A | 10/2000 |
|---|---|---|
| CN | 104560753 A | 4/2015 |
| CN | 106191099 A | 12/2016 |
| CN | 107746815 A | 3/2018 |
| WO | 2004016726 A2 | 2/2004 |

OTHER PUBLICATIONS

Jie ("Preliminary analysis of gene expression and proteomic change of the recombined yeast N6076 obtained by low-energy nitrogen ion beam implantation", Genomics and Applied Biology, 2017, vol. 36 No. 11 4678-4685, Abstract Provided) (Year: 2017).*
By VanDusen ("Adenine Quantitation in Yeast Extracts and Fermentation Media and Its Relationship to Protein Expression and Cell Growth in Adenine Auxotrophs of *Saccharomyces*" Biotechnol. Prog. 1997, 13 1-7). (Year: 1997).*
International Search Report issued on Sep. 24, 2020 for related PCT/CN2020/095553 filed Jun. 11, 2020.
Written Opinion issued on Sep. 24, 2020 for related PCT/CN2020/095553 filed Jun. 11, 2020.
Semkiv, M. V., etc. Increased ethanol accumulation from glucose via reduction of ATP level in a recombinant strain of *Saccharomyces cerevisiae* overexpressing alkaline phosphatase BMC biotechnology May 15, 2014 (May 15, 2014) Issue 42 vol. 14 ISSN: 1472-6750 pp. 1-9.
Clare, J. et al. Nucleotide sequence of a yeast Ty element: evidence for an unusual mechanism of gene expression Proceedings of the National Academy of Sciences of the United States of America May 31, 1985(May 31, 1985) Issue 9 vol. 82 ISSN: 0027-8424 pp. 2829-2833.

(Continued)

*Primary Examiner* — Robert J Yamasaki
*Assistant Examiner* — Charles Zoltan Constantine
(74) *Attorney, Agent, or Firm* — HAUPTMAN HAM, LLP (57) ABSTRACT

The invention discloses a genetically engineered bacterium in which the gene encoding adenine deaminase on the genome of the bacterium is knocked out or/and the gene encoding the enzyme in the NAD$^+$ anabolic pathway is integrated on the genome of the bacterium. The invention also discloses a construction method of the above-mentioned genetically engineered bacteria. The gene encoding adenine deaminase on the genome of the host strain is knocked out to obtain a strain with high NAD$^+$ yield. Or the expression cassettes of the gene encoding the enzyme in the NAD$^+$ synthesis pathway are constructed separately, and then the enzyme encoding The gene expression cassette is integrated into the genome of the host strain whose gene encoding adenine deaminase is knocked out to construct a strain with high NAD$^+$ production. The application of the above genetically engineered bacteria is disclosed. A method of producing NAD$^+$ is disclosed.

5 Claims, 3 Drawing Sheets
Specification includes a Sequence Listing.

(56) References Cited

OTHER PUBLICATIONS

Deeley M. C. Adenine deaminase and adenine utilization in *Saccharomyces cerevisiae* Journal of bacteriology May 31, 1992 (May 31, 1992) No. 10 vol. 174 ISSN: 0021-9193 p. 3102-3110.
Preservation Certificate of Biomaterial (strain) of reference: KH08; China General Microbiological Culture Collection Center (CGMCC); CGMCC No. 19048; Beijing, China; Dec. 11, 2019; 2 pgs. (Attachments 1 and 2 noted in Oct. 20, 2023 response.).

\* cited by examiner

GENETICALLY ENGINEERED BACTERIA, ITS CONSTRUCTION METHOD AND ITS APPLICATION IN PRODUCING NAD+ METHOD

RELATED APPLICATIONS

This is a U.S. national stage of international application No. PCT/CN2020/095553 filed on Jun. 11, 2020, which claims priority from China Patent Application No. 201911326087.0 filed on Dec. 20, 2019, the entire content of which is incorporated by reference.

BACKGROUND OF THE INVENTION

1. Technical Field

The present invention relates to a genetically engineered bacteria, its construction method and its application in producing NAD+ method, which belongs to the field of bio-technology.

2. Background Art

Coenzyme I, also known as Nicotinamide adenine Dinucleotide (NAD+), is a coenzyme of many dehydrogenases in the body, which connects the tricarboxylic acid cycle and the respiratory chain to realize the transfer of electrons. NAD+ is involved in various physiological activities such as cell material metabolism, energy synthesis, cell DNA repair, and signal transmission, and plays an irreplaceable role in glycolysis, gluconeogenesis, tricarboxylic acid cycle and respiratory chain. Its structural formula is as follows:

2.1

Beginning from the 1840s when NAD+ was discovered the first time, researchers have increasingly focused on the exploration of NAD+ in angiogenesis, gene repair, anti-aging, and reduction of birth defects, etc., making NAD+ show vitality in the field of anti-aging and medicine. NAD+ is not conducive to the absorption of human body because of its relatively large molecular weight, supplementing its precursor nicotinamide mononucleotide (NMN) or nicotinamide ribose (NR) may be the most scientific and effective way to supplement for NAD+. NAD+ can cross the blood-brain barrier whereas NMN and NR cannot, which makes NAD+ irreplaceable in the treatment of addiction and other brain disorders. NAD+ can be used for the treatment of chronic diseases, weight control, mood disorders, alcohol and drug addiction diseases as well as the prevention of liver damage, multiple sclerosis autoimmune neurodegeneration, heart damage caused by heart disease, stroke, brain damage caused by injury.

There are some methods for the synthesis of NAD+: de novo synthesis route, several remedial routes starting with nicotinamide mononucleotide, nicotinamide ribose, nicotinamide or niacin, etc. However, the de novo synthesis route has limited the yield of NAD+. Therefore, the NAD+ industrial production mostly begins from the salvage process or NAD+ nucleotide precursor nicotinamide mononucleotide, nicotinamide ribose, nicotinamide or nicotinic acid, using enzymatic or whole cell transformation method to produce the NAD+. Biological enzymatic methods such as: starting from nicotinamide, nicotinamide mononucleotide is obtained under the action of nicotinamide phosphoribosyltransferase, and then NAD+ is obtained under the catalization of nicotinamide mononucleotide and nicotinamide phosphoribosyltransferase. Some nicotinamide mononucleotide also starts with nicotinamide ribose under the action of nicotinamide ribokinase, and then which reacts to obtain NAD+. But this way needs prepare a variety of enzyme solution resulting in cumbersome processes and a relatively high cost of industrialization. Otherwise the synthesis of NAD+ starts directly from chemically synthesized nicotinamide mononucleotide which is catalyzed by enzyme. But the synthetic method has high cost and the problem of chiral compounds due to the chemical synthesis of nicotinamide mononucleotide. It has been reported to produce NAD+ by using of yeast (Sakai, T., et al. Accumulation of nicotinamide adenine dinucleotidein Baker's Yeast by secondary culture. Agr. Biol. Chem., 37 (5), 1049-1056, 1973), *Corynebacterium ammoniagenes* (Elhariry, H. M., et al. S434F in NrdE generates the thermosensitive phenotype of *Corynebacterium ammoniagenes* CH31 and enhances thermolability by increasing the surface hydrophobicity of the NrdE(Ts) protein. Appl. Environ. Microbiol. 71 (9), 5582-5586, 200), and *bacillus* et al., produce NAD+ by whole-cell conversion of substances such as nicotinamide and adenine, but the yield is low, resulting in high production cost.

SUMMARY OF THE INVENTION

Based on the technical problems of the background technology, the invention proposes a genetically engineered bacteria, its construction method and its application in producing NAD+ method. A strain with high NAD+ yield is obtained by knocking out the encoding gene of adenine deaminase in host strain genome or integrating the expression cassettes of the genes encoding the enzymes into the host strain genome.

The invention have proposed a genetically engineered bacteria that is the encoding gene of adenine deaminase in genome of strain is knocked out, or/and that enzyme coding gene in NAD+ synthesis process incorporates the genome of strain.

What the above-mentioned the encoding gene of adenine deaminase is knocked out will completely lose or weaken the activity of adenine deaminase.

Preferably, the strain is *Saccharomyces cerevisiae*

Preferably, the enzyme in the NAD+ synthesis process is at least one of the nicotinamidase PNC1, Nicotinate phosphoribosyl transferase NPT1, Nicotinic acid mononucleotide adenylyl transferase NMA1, Nicotinic acid mononucleotide adenylyl transferase NMA2, and Glutamine-dependent NAD(+) synthetase QNS1.

The above-mentioned NMA1 and NMA2 are isoenzymes.

Preferably, the enzyme in the NAD$^+$ synthesis process is at least one of the Nicotinate phosphoribosyl transferase NPT1, Nicotinic acid mononucleotide adenylyl transferase NMA1.

Preferably, the invention have provided a genetically engineered bacteria which is *Saccharomyces cerevisiae* KH08, integrating the Nicotinate phosphoribosyl transferase NPT1 and Nicotinic acid mononucleotide adenylyl transferase NMA1 of NAD$^+$ synthetic process on its genome, whose encoding gene of adenine deaminase in genome has been knocked out to obtain a strain with high NAD$^+$ yield. *Saccharomyces cerevisiae* KH08 is deposited in Comprehensive Microbiology Center of China Microbial Culture Collection Management Committee CGMCC, and its deposit number is CGMCC No. 19048.

The invention also discloses a method for constructing the above-mentioned genetically engineered bacteria which is that the encoding gene of adenine deaminase in host strain genome is knocked out to obtain a strain with high NAD$^+$ yield;

Or constructing the expression cassettes of the genes encoding the enzymes in the NAD$^+$ synthesis process respectively, and then integrating the expression cassettes of the genes encoding the enzymes into the host strain genome to construct a strain with high NAD$^+$ yield.

Or constructing the expression cassettes of the genes encoding the enzymes in the NAD$^+$ synthesis process respectively, and then integrating the expression cassettes of the genes encoding the enzymes into the host strain genome whose genes encoding adenine deaminase have been knocked out to construct a strain with high NAD$^+$ yield.

The method of "constructing the expression cassettes of the genes encoding the enzymes in the NAD$^+$ synthesis process" is that the genes encoding enzymes in the NAD$^+$ synthesis pathway is ligated into the expression frame of the integrated plasmid of the host strain.

The above-mentioned integrated plasmid contains components: pMB1 replicon, ampicillin resistance encoding gene, G418 resistance selection marker KanMX, δ1 fragment, δ2 fragment, GPD promoter, ADH1 terminator, TEF1 promoter and CYC1 terminator. The integrated plasmid is referred to as plasmid pND04 for short.

Preferably, the integration is a δ-site integration method.

Preferably, the δ sequence comprises a M fragment and a δ2 fragment, and the nucleotide sequence of the δ1 fragment is shown in SEQ ID No. 1, and the nucleotide sequence of the δ2 fragment is shown in SEQ ID No.2.

The δ sequence is the long terminal repeat sequence on the Ty transposon. They are located on the retrotransposons Ty1 and Ty2 of the chromosomal DNA of *Saccharomyces cerevisiae*. δ-site integration is a way of gene integration using δ sequence homology. There is a statement about δ sequence (Semkiv, M. V., et al. Increased ethanol accumulation from glucose via reduction of ATP level in a recombinant strain of *Saccharomyces cerevisiae* overexpressing alkaline phosphatase. BMC Biotechnol 42(14), 2014). The integration of genes that need to be overexpressed into *Saccharomyces cerevisiae* can increase the stability of genes during fermentation.

The above-mentioned host strain is *Saccharomyces cerevisiae*, which is bought from Yantai Mauri Yeast Co., Ltd. NO. YT201902260569. We rename this strain *Saccharomyces cerevisiae* KH01.

The invention also proposes the application of the above-mentioned genetic engineering bacteria in the production of NAD$^+$.

The invention also proposes a method for producing NAD$^+$ which uses nicotinamide or/and adenine as a substrate and the genetically engineered bacteria to produce NAD$^+$.

Figure 1:
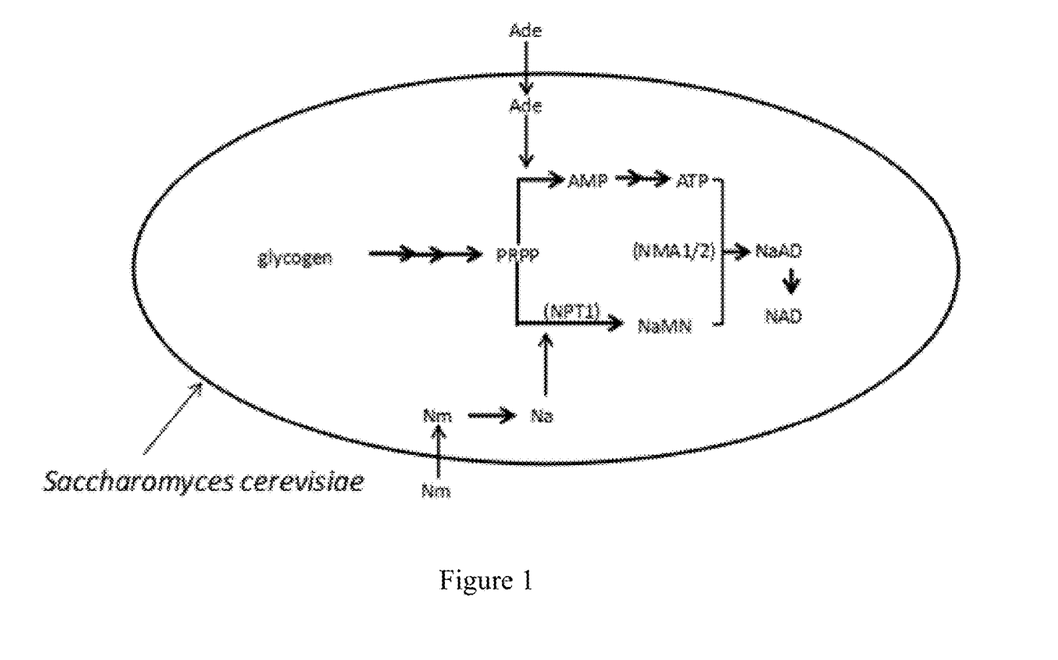
FIG. 1 is a schematic diagram of yeast whole cell transformation of NAD In the figure, glycogen is glycogen reserve, *Saccharomyces cerevisiae* is *Saccharomyces cerevisiae* cell, Nm is nicotinamide, Na is niacin, Ade is adenine, PRPP is 5-phoshoribose-1-pyrophosphate, AMP is 5-monophosphate Adenosine, ATP is adenosine 5-triphosphate, NaMN is nicotinic acid ribose monophosphate, NaAD is nicotinic acid adenine dinucleotide, NAD is nicotinamide adenine dinucleotide, NPT1 is Nicotinate phosphoribosyl transferase, NMA1 is Nicotinic acid mononucleotide adenylyl transferase 1 and NMA2 is Nicotinic acid mononucleotide adenylyl transferase 2.

The above mentioned nicotinamide or/and adenine as a substrate and the genetically engineered bacteria to produce the NAD$^+$ is referring to the FIG. 1.

THE INVENTION HAS THE ADVANTAGES OF

1. The invention integrates the coding gene of the enzyme in the NAD$^+$ synthesis pathway into the genome of the strain, especially Nicotinate phosphoribosyl transferase NPT1 and Nicotinic acid mononucleotide adenylyl transferase NMA1, which can greatly improve the ability of yeast to transform into NAD$^+$. After fermentation, adding nicotinamide or/and adenine directly to the fermentation broth for whole cell transformation can qualitatively increase the NAD$^+$ content in the yeast cell.

2. When NAD$^+$ is produced using adenine as a substrate, adenine produces a large amount of secondary hypoxanthine byproducts, which increases the difficulty of purification of NAD$^+$. Therefore, knocking out the gene encoding adenine deaminase in the strain genome makes the activity of adenine deaminase weakened even completely lost, which can reduce the amount of substrate adenine and alleviate the impact of hypoxanthine by-products on subsequent purification. Compared with wild-type yeast, the genetically engineered bacteria of the invention during producing the same amount of NAD$^+$, the amount of adenine is reduced by at least 3 times, and the accumulation of hypoxanthine is reduced by at least 6 times.

3. Integrating the encoding gene of the enzyme in the NAD$^+$ synthesis process into the host genome, whose encoding gene is knocked out adenine deaminase, can increase the production of NAD$^+$, reduce the amount of substrate adenine, alleviate the impact of hypoxanthine by-products on subsequent purification, and reduce costs. Compared with wild-type yeast, the yield of NAD$^+$ is increased by more than 80%.

Biological Preservation Instructions

*Saccharomyces cerevisiae* KH08 was deposited in Microbiology Center of China Microbial Culture Collection Management Committee CGMCC in Beijing, addressed in No. 3, Yard. 1, Beichen West Road, Chaoyang District, Beijing, 100101, China, on Nov. 28, 2019. The deposit number is CGMCC NO. 19048, and its morphology and physical and chemical properties are as follows:

Colony color: milky white; growth temperature: 28-30° C.; optimum pH: 5.0-6.0; colony morphology: the surface is smooth, moist, sticky, easy to pick up, uniform texture; reproduction mode: budding reproduction.

DESCRIPTION OF PREFERRED EMBODIMENTS

The detailed implementation of the invention is further described as follows. The following embodiments are used to illustrate the invention, but not to limit the scope of the invention.

Except for special instructions, the experimental methods used in the following embodiments are all conventional methods. Except for special instructions, the materials and reagents etc. used in the inventation can be obtained from commercial sources.

In the following embodiments, NPT1, NMA1, and AAH1 all represent genes, and NPT1, NMA1, and AAH1 all represent enzymes.

The source information of the preferred embodiments, reagents and plasmids used in the examples are as follows: Agarose gel DNA recovery kit (upgraded spin column type) (Shanghai Generay Bioengineering Co., Ltd., catalog number GK2043-200); GB clonart seamless cloning reagent Kit (Suzhou Shenzhou Gene Co., Ltd., Item No. GB2001-48); Yeast Genomic DNA Extraction Kit (Beijing Kangwei Century Biotechnology Co., Ltd., Item No. CW0569); Plasmid pUC57 (Wuhan Miaoling Biotechnology Co., Ltd., Item No. P0087); pUG6 plasmid (Wuhan Miaoling Biotechnology Co., Ltd., item number P0104); pSH65 plasmid (Wuhan Miaoling Biotechnology Co., Ltd., item number P1352); SmaI, SdaI and other restriction endonucleases (Thermo Fisher Technology (China) Co., Ltd. Company).

Example 1

The construction of δ integrated expression plasmid in Saccharomyces cerevisiae is presented as the follows:

1 the Construction of Integrated Plasmid Containing Delta Sequence 1.1 Using the Saccharomyces cerevisiae genome as a template, amplify PCR to get 235 bp fragment I and 281 bp fragment II by the primers listed in Table 1 respectively. And the fragment I contains a 154 bp δ1 fragment whose sequence is shown in SEQ ID No. 1. The fragment II contains a a 180 bp δ2 fragment whose sequence is shown in SEQ ID No.2.

1.2 Using plasmid pUC57 as a template, amplify PCR to get the fragment pUC57 of 2682 bp by the primers listed in Table 1.

1.3 The fragment pUC57, fragment I and fragment II are gel recovery disposed by using agarose gel DNA recovery kit, and then which was seamlessly cloned by GBclonart seamless cloning kit to construct the plasmid pND04.

TABLE 1

Sequences of primers used in steps 1.1 and 1.2

| Fragment | Primer name | Primer sequence (5'-3') |
| --- | --- | --- |
| pUC57 fragment | pUC-F<br>pUC-R | GTTCCATCCCAATACGCGTCAATTCACTG<br>GTTCCATCCCAATGGCGCGCCGAG |
| Fragment I | delta-F1<br><br>delta-R1 | GAATTGACGCGTATTGGGATGGAACGCGGCCGCGT<br>TTAAACTGTTGGAATAGAAATCAACTATC<br>TCATCATTTTATATGTTTATATTCACCCGGGCCTGC<br>AGGTTGATCCTATTACATTATCAATCC |
| Fragment II | delta-F2<br><br>delta-R2 | AGGATTGATAATGTAATAGGATCAACCTGCAGGCC<br>CGGGTGAATATAAACATATAAAATGATG<br>GCTCGGCGCGCCATTGGGATGGAACGCGGCCGCGT<br>TTAAACTGAGAAATATGTGAATGTTGAG |

2. The Construction of Integrated Plasmid Containing Dual Promoters

Plasmid pNL01, the nucleotide sequence of which is shown in SEQ ID No. 3. And plasmid pNL01 contains GPD promoter and TEF1 promoter.

Using the plasmid pNL01 as a template, amplify PCR to get 1811 bp dual promoter fragment by primers pND05-F1 and pND05-R1. The dual promoter fragment is gel recovery disposed by using agarose gel DNA recovery kit, and then which was seamlessly cloned together with plasmid pND04 recovered by digestion with SmaI (using GB clonart seamless cloning kit) to construct the plasmid pND05.

TABLE 2

Sequences of primers pND05-F1 and pND05-R1

| Primer name | Sequence (5'-3') |
| --- | --- |
| pND05-F1 | TGTAATAGGATCAACCTGCAGGCCCGTTAGCATATCTAC<br>AATTGGGTGAAATG |
| pND05-R1 | TCATTTTATATGTTTATATTCACCCCCATGGGTTGGCCG<br>ATTCATTAATGCAG |

3. The Construction of Integrated Plasmid Containing Yeast Selection Markers

Using the pUG6 plasmid as a template, amplify PCR to get KanMX fragment of 1654 bp by primers pND06-F1 and pND06-R1. The KanMX fragment is gel recovery disposed by using agarose gel DNA recovery kit, and then which was seamlessly cloned together with plasmid pND05 recovered by digestion with SdaI (using GBclonart seamless cloning kit) to construct the plasmid pND06.

TABLE 3

Sequences of primers pND06-F1 and pND06-R1

| Primer name | Sequence (5'-3') |
|---|---|
| pND06-F1 | TAATGTAATAGGATCAACCTGCAGGTTAATTAACTGCAGGTCGACAACCCTTAATATAAC |
| pND06-R1 | TTGTAGATATGCTAACGGGCCTGCAATTTAAATCACTAGTGGATCTGATATCACCTAATAAC |

4. The Construction of Integrated Plasmid Containing the Target Gene.

4.1 Using the plasmid pND06 as a template, amplify PCR to get the vector fragment 1 of 6391 bp by primers pEZTEF1-F1 and pEZTEF1-R1.

4.2 Using the *Saccharomyces cerevisiae* genome as a template, amplify PCR to get the NPT1 fragment of 1347 bp by primers NPT1-F1 and NPT1-R1.

4.3 The vector fragment 1, fragment NPT1 are gel recovery disposed by using agarose gel DNA recovery kit, and then which was seamlessly cloned by GBclonart seamless cloning kit to construct the plasmid pND07.

4.4 Using the plasmid pND07 as a template, amplify PCR to get the vector fragment 2 of 7678 bp by primers pEZGPD-F1 and pEZGPD-R1.

4.5 Using the *Saccharomyces cerevisiae* genome as a template, amplify PCR to get the NMA1 fragment by primers NMA1-F1 and NMA1-R1.

4.6 The vector fragment 2, fragment NMA1 are gel recovery disposed by using agarose gel DNA recovery kit, and then which was seamlessly cloned by GBclonart seamless cloning kit to construct the plasmid pND08 of which nucleotide sequence is shown in SEQ ID No.4.

Figure 2:
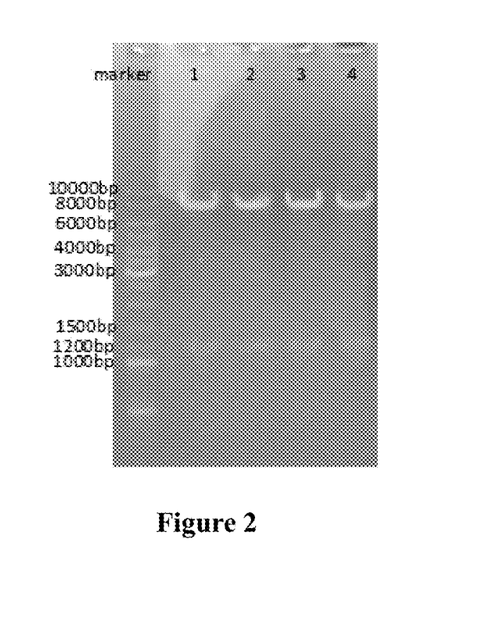
FIG. 2 is a nucleic acid gel image verified by Eco105I digestion of plasmid pND08.

4.7 The plasmid pND08 was verified by restriction digestion, and the results are shown in FIG. 2. FIG. 2 is the nucleic acid gel map of the Eco105I digestion verification of plasmid pND08. In the FIG. 2, 1, 2, 3, 4 are pND08 plasmids, and the marker is Thermo Scientific GeneRuler DNA Ladder Mix (Product No. SM0333). It can be seen from FIG. 2 that 1309 bp and 7574 bp bands could be obtained after plasmid pND08 was digested with Eco105I enzyme, and plasmid pND08 was verified to be correct.

TABLE 4

Sequences of primers used in 4.1, 4.2, 4.4 and 4.5

| Primer name | Primer sequence (5'→3') |
|---|---|
| pEZTEF1-F1 | GAATTCTGCAGATATCCATCACACTG |
| pEZTEF1-R1 | TTTGTAATTAAAACTTAGATTAGATTGCTATGC |
| NPT1-F1 | ATCTAATCTAAGTTTTAATTACAAAGGATCCATGTCAGAACCAGTGATAAAGTCTC |
| NPT1-R1 | AGTGTGATGGATATCTGCAGAATTCTTAGGTCCATCTGTGCGCTTC |
| pEZGPD-F1 | ACCCGGGGCGAATTTCTTATG |
| pEZGPD-R1 | TTTGTTTGTTTATGTGTGTTTATTCGAAACTAAG |
| NMA1-F1 | GAATAAACACACATAAACAAACAAAATGGATCCCACAAGAGCTCC |
| NMA1-R1 | AAATCATAAGAAATTCGCCCCGGGTTCATTCTTTGTTTCCAAGAACTTGCTTAAC |

Example 2

Knockout of AAH1 Gene in *Saccharomyces cerevisiae* (Diploid):

The adenine deaminase expressed by the AAH1 gene can degrade adenine into less soluble hypoxanthine, which affects the subsequent purification work and causes the waste of adenine. Therefore, knockout of AAH1 gene can reduce both the amount of adenine and the amount of hypoxanthine, a by-product to achieve the purpose of reducing costs.

There are two AAH1 alleles in diploid yeast, and it is too inefficient to replace only one of them, so the two alleles need to be knocked out separately. When two alleles are knocked out separately, homologous arms used for two knockouts should be designed to avoid the occurrence of two knockouts at the same location. The specific operation is as follows:

1. Knockout of the First AAH1 Gene 1.1 Using the plasmid pUG6 as a template, PCR amplification was performed with primers AAH1-F1 and AAH1-R1, and then gel recovery was performed with agarose gel DNA recovery kit to obtain 1588 bp AAH1 knockout fragment I.

1.2 Preparation of *Saccharomyces cerevisiae* competent cells of *Saccharomyces cerevisiae* KH01 (This is a strain for host which is *Saccharomyces cerevisiae* purchased from Yantai Marley Yeast Co., Ltd., and its batch number is YT201902260569. This strain is renamed *Saccharomyces cerevisiae* KH01). A ring of bacterial liquid was taken from the glycerol cryopreserved tube, and it was marked and activated on YPD plate (the composition of YPD medium was: yeast powder 10 g/L, peptone 20 g/L, and glucose 20 g/L). It was placed in an incubator at 30° C. for 3 days. And then pick a single colony from the YPD plate and inoculate it into a 4 mL YPD test tube, and incubate it at 30° C. and 250 rpm for 16 hours. And then transfer the test tube bacterial solution to a 30 mL YPD shake flask at a 2% inoculum amount, and incubate it at 30° C. and 250 RPM under culture to the $OD_{600}$=0.8-1.2. By collecting bacteria, with cold aseptic water washing twice, reoccupying cold 1 M sorbitol after washing twice, bacteria with 1 M sorbitol finally hanging weight to 300 uL, we get Saccharomyces cerevisiae competent cells which are divided into three equal parts by 100 μL per and place them in ice for later use.

1.3 Electro transformation: Take 1 μg of AAH1 knock-out fragment I and add it to 100 μL of Saccharomyces cerevisiae competent cells, then place them in ice for a while, and transfer them to a 2 mm electric rotor cup in an ice bath. After 1.5 KV electric shock, resuspend in 1 mL YPD medium and transfer to EP tube and incubate at 30° C. in a shaker for 1-3 h to obtain the transformation solution. Take 200 μL and 300 μL of the transformation solution respectively to replace them on YPD plates containing 500 mg/L G418 antibiotics, and place them in a 30° C. incubator for 3-5 days to obtain transformants, cultivate in a 30° C. incubator for 3-5 days to obtain transformants, pick the transformants and streak for purification, extract the genome with the yeast genome extraction kit, perform PCR with primers on AAH1-500F/AAH1-500R to verify that the knockout is correct, this transformant strain was named Saccharomyces cerevisiae KH07SG (containing G418 resistance).

3. Knockout of the Second AAH1 Gene (Knockout of the Second AAH1 Gene in S. cerevisiae KH07S)

3.1 Using the plasmid pNL01 as a template, amplify PCR with primers AAH1-F2 and AAH1-R2. Then use agarose gel DNA recovery kit for gel recovery to obtain 1589 bp AAH1 knockout fragment II.

3.2 Prepare competent cells of KH07S strain according to the step 1.2 in Example 2.

3.3 Transform the AAH1 knock-out fragment II into KH07S strain cells to obtain the transformant according to the step 1.3 in Example 2. Take the transformant for streak purification and extract the genome, use primers to perform PCR on AAH1-500F/AAH1-500R to verify that the knockout is correct, and name the transformant strain Saccharomyces cerevisiae KH07G (containing G418 resistance).

TABLE 6

Sequences of primer AAH1-F2 and AAH1-R2

| Primer name | Sequence (5'→3) |
|---|---|
| AH1-F2 | TTATTTTGAAATAATAACTACCATTAGAACTAACAAAAGAA AAGAAAAAAAAAATAATGGTTTCTGTGGAGCTGCAGGTCGA CAACCCTTAATATAAC |
| AH1-R2 | CTAATGCGAATATTTAGTGACTACTTCGTCCACTCTACTTA ACAAACCGTTCTTTCTTTTATCGTCACACCACTAGTGGATC TGATATCACCTAATAAC |

TABLE 5

Primers used for knockout of the first AAH 1 gene

| rimer name | Sequence (5'→3) |
|---|---|
| AH1-F1 | CGACATCTTTTGCAAATGAATAATTGACAAGCAGGCCTGTGT ATTTATAGCTGCAGGTCGACAACCCTTAATATAAC |
| AH1-R1 | ATCGAAAAAGACTTTCAACAAAAATATTATACAATGTCTTGC AAATGGTACACTAGTGGATCTGATATCACCTAATAAC |
| AH1-500F | GATGACTTTAACTGTGCACAC |
| AH1-500R | GACTCGCCTTCAGAAAATG |

2 KH07SG Strain Elimination

According to the method 1.2 in Example 2, prepare competent cells of Saccharomyces cerevisiae KH07SG strain. According to the method 1.3 in Example 2, transform 500 ng of pSH65 plasmid into competent cells of Saccharomyces cerevisiae KH07SG strain to obtain a transformation solution. Coat the transformation solution on YPD with 30 mg/L zeo or YPD with 15 mg/L Phleo. After culturing in a 30° C. incubator for 3 days, pick the transformants and inoculate YPG (with 20 g/L galactose instead of 20 g/L glucose, the others are the same as YPD medium) test tube, culture for 2-3 h at 30° C., 250 rpm. After the bacterial solution is diluted, take 100 μL each of the bacterial solution of different dilutions and spread on the YPD plate and culture in an incubator at 30° C. for 3 days. A single colony YPD plate and YPD plate containing 500 mg/L G418 antibiotic were selected respectively. The resistant strain is screened out (the strain grows on the YPD plate and does not grow on the YPD plate containing 500 mg/L G418 antibiotic), and the strain is named Saccharomyces cerevisiae KH07S.

Figure 3:
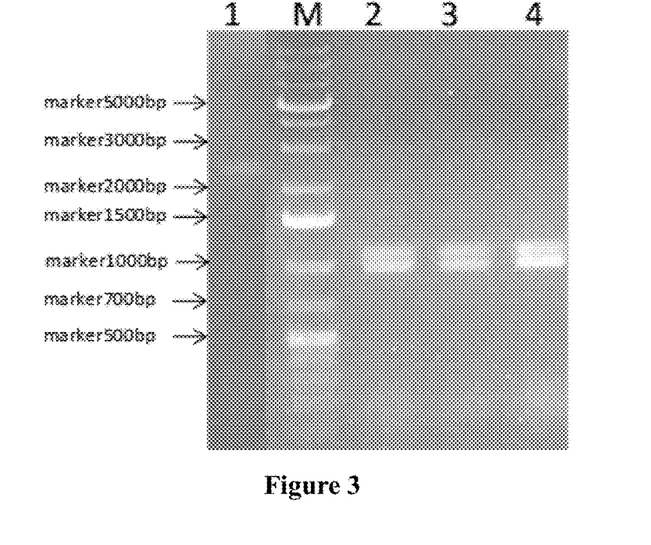
FIG. 3 shows the nucleic acid gel image verified by PCR of Saccharomyces cerevisiae KH07 strain. In the figure, 1 is the genome of Saccharomyces cerevisiae KH01 strain, 2, 3, and 4 are the genomes of Saccharomyces cerevisiae KH07 strain, and M is Marker.

4. According to the step 2 in Example 2, the strain of Saccharomyces cerevisiae KH07G was eliminated to obtain the correctly eliminated strain which was named Saccharomyces cerevisiae KH07. The primer pair AAH1-500F/AAH1-500R in Table 5 was used to perform PCR confirmation of the Saccharomyces cerevisiae KH07 strain. The results are shown in FIG. 3. FIG. 3 is the nucleic acid gel image verified by the Saccharomyces cerevisiae KH07 strain. wherein 1 is the genome of Saccharomyces cerevisiae KH01 strain, 2, 3 and 4 are the genome of Saccharomyces cerevisiae KH07 strain, and M is Marker which is Thermo Scientific GeneRuler the DNA. 1 kB Plus Relay Ladder Logic (NO: SM1332). FIG. 3 shows that The Saccharomyces cerevisiae KH01 strain has a 2031 bp band of interest, while the Saccharomyces cerevisiae KH07 strain has two bands of 1011 bp and 1151 bp, and the double knockout and elimination of the AAH1 gene of the Saccharomyces cerevisiae KH07 strain is correct.

5. Testing 5.1 Take the Saccharomyces cerevisiae strains KH01, KH07S and KH07 and use the same shake flask fermentation method to produce $NAD^+$ to verify the effect of gene knockout.

The method of producing $NAD^+$ by shaking flask fermentation is to pick a ring of bacteria liquid from the glycerol cryopreservation tube of *Saccharomyces cerevisiae* to streak YPD plate, place it in a 30° C. incubator, and cultivate it for 2-3 days, use an inoculating loop to pick the activated single clone of *Saccharomyces cerevisiae* into a 500 mL shake flask containing 50 mL fermentation medium (Fermentation medium formula: glucose 50 g/L, casein extract 15 g/L, yeast extract 15 g/L, NaCl 5 g/L, $KH_2PO_4$ 1 g/L, $K_2HPO_4$ 1 g/L, $MgSO_4 \cdot 7H_2O$ 0.3 g/L, pH 5.4). After 72 hours of culture at 30° C. and 250 rpm, adenine and nicotinamide were added to make the final concentration of adenine 3 g/L and the final concentration of nicotinamide 6 g/L. The culture was continued at 30° C. and 250 RPM for 72 hours, and the fermentation was stopped to obtain the fermentation broth.

Fermentation extract: 20 mL of the above fermentation liquid was centrifuged in a 50 mL centrifuge tube to collect the bacteria, and 5 mL 0.2% formic water was added into the bacteria, which was mixed in vortex. The bacteria were then stirred at 1000 RPM for 5 min and quickly transferred to an ice bath at 95° C. The mixture was then stirred at 1000 RPM for 5-10 min and centrifuged at 7500 RPM for 5 min.

Detection: The contents of adenine, hypoxanthine and $NAD^+$ in the fermented extract were detected by HPLC. The detection method was as follows: 1 mL of $NAD^+$ extract was absorbed and filtered by a 0.22 m filter membrane for sampling detection.

Figure 4:
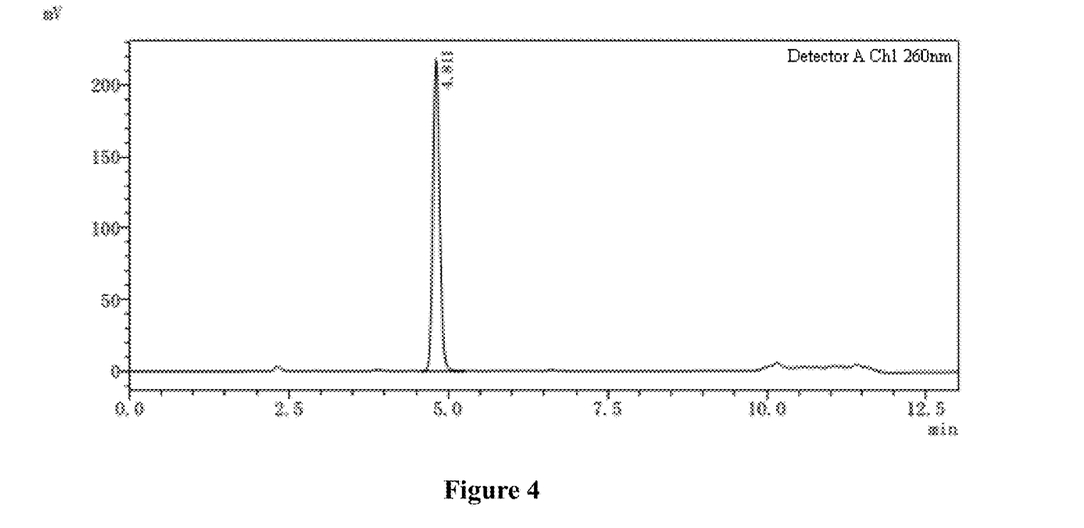
FIG. 4 shows the HPLC chromatogram of $NAD^+$.
Figure 5:
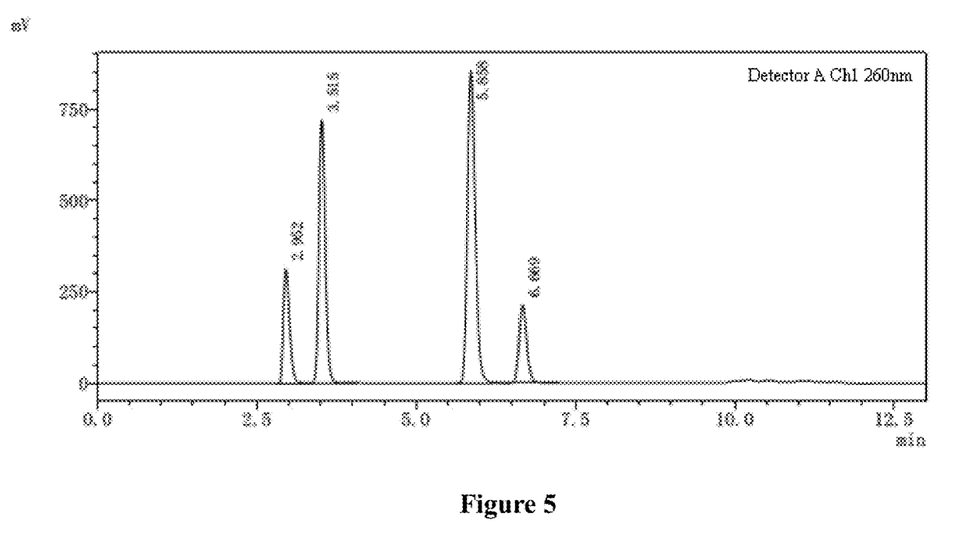
FIG. 5 shows the HPLC chromatograms of niacin, hypoxanthine, adenine and nicotinamide.

The detection conditions of HPLC were as follows: the chromatographic column was Waters C18 (4.6×150 mm, 5 m), and the uv detector was used for detection, with the wavelength=260 nm, flow rate=1.0 mL/min, injection volume=5 L, column temperature=30° C., mobile phase A was methanol, mobile phase B was 10 mM ammonium acetate aqueous solution (pH=5.0), gradient elution, elution procedure is shown in Table 7. See FIG. 4 and FIG. 5 for typical chromatograms. FIG. 4 is HPLC for $NAD^+$. FIG. 5 is HPLC for niacin, hypoxanthine, adenine and nicotinamide. It can be seen from FIG. 4 that the retention time of $NAD^+$ is 4.811 min. As can be seen from FIG. 5, the retention time of niacin, hypoxanthine, adenine and niacinamide was 2.952 min, 3.515 min, 5.858 min and 6.669 min respectively.

TABLE 7

| Time (min) | Mobile phase A (v/v %) | Mobile phase B (v/v %) |
|---|---|---|
| 0.00-0.01 | 2 | 98 |
| 0.01-7.00 | 7 | 93 |
| 7.00-8.00 | 80 | 20 |
| 8.00-9.00 | 80 | 20 |
| 9.00-9.10 | 2 | 98 |
| 9.10-13.00 | 2 | 98 |

Results: In the fermentation extract, the contents of adenine and hypoxanthine in the cells of strains KH01, KH07S and KH07 were shown in Table 8:

TABLE 8

| *Saccharomyces cerevisiae* strains | Adenine (mg/L) | Hypoxanthine (mg/L) |
|---|---|---|
| KH01 | 6.11 | 127.23 |
| KH07S | 9.94 | 117.34 |
| KH07 | 379.87 | 20.46 |

As can be seen from Table 8, double knockout of AAH1 gene can significantly reduce the degradation of adenine to hypoxanthine, and the accumulation of hypoxanthine is reduced by at least 6 times.

Example 3

*Saccharomyces cerevisiae* Strain KH01 Integrating the NPT1 and NMA1 Genes:

The plasmid pND08 prepared in Example 1 was double-cut with MssI single enzyme, and then recovered with agarose gel DNA recovery kit to obtain 6178 bp integrated fragment.

According to steps 1.2 and 1.3 in Example 2, the 6178 bp integral fragment was transformed into the cell of *Saccharomyces cerevisiae* KH01 to obtain the transformants. The transformants were scribed and purified, and then the transformants were screened by flask fermentation method in 5.1 of Example 2 to produce $NAD^+$, and the dominant transformants with high yield of $NAD^+$ were obtained. The transformants were named *Saccharomyces cerevisiana* KH06 after elimination in step 2 of Example 2.

Testing: *Saccharomyces cerevisiae* KH06 was selected to produce $NAD^+$ by flask fermentation in 5.1 of Example 3, and the results were compared with *Saccharomyces cerevisiae* KH01, as shown in Table 10.

TABLE 10

| different strains of the $NAD^+$ yield | |
|---|---|
| Strain | $NAD^+$ (g/kg DCW) |
| KH01 | 11.3 |
| KH06 | 20.5 |

As can be seen from Table 10, the $NAD^+$ yield of *Saccharomyces cerevisiae* KH06, which overexpressed the genes NPT1 and NMA1, was more than 80% higher than that of *Saccharomyces cerevisiae* KH01.

Example 4

*Saccharomyces cerevisiae* KH07 Integrating NPT1 and NMA1 Genes

According to the steps in Example 3, the 6178 bp integration fragment was transformed into the cells of *Saccharomyces cerevisiae* KH07 to obtain transformants. The transformants were purified, and then the transformants were screened by flask fermentation method in 5.1 of Example 2 to produce $NAD^+$, and the dominant transformants with high yield of $NAD^+$ were obtained. The constriction strain was named *Saccharomyces cerevisiae* KH08 after eliminating resistance as described in Example 2 which was preserved in CGMCC, General Microbiology Center of China Microbial Species Preservation Management Committee, the preservation number is CGMCC No. 19048.

Testing: According to the method of shake flask fermentation to produce $NAD^+$ in 5.1 of Example 2. The single colony of *Saccharomyces cerevisiae* KH08 was inoculated in a 500 mL flask containing 50 mL fermentation medium, and cultured at 30° C., 250 RPM for 72 h, adenine and nicotinamide were added, and the final concentration of adenine and nicotinamide was 0.8 g/L and 6 g/L respectively. The culture was continued at 30° C. and 250 RPM for 72 h, and then the fermentation was stopped to obtain the fermentation liquid. The *S. cerevisiae* KH07 was used as the control, and the fermentation results were shown in Table 11.

TABLE 11

NAD+ production of different strains

| Strain | NAD+ (g/kg DCW) |
|---|---|
| KH07 | 12.0 |
| KH08 | 21.5 |

As can be seen from Table 11, the NAD+ yield of Saccharomyces cerevisiae KH08 strain with NPT1 and NMA1 overexpressed was about 80% higher than that of Saccharomyces cerevisiae KH07.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are Within the scope as defined in the appended claims.

What is claimed is:

1. A method for producing a NAD+ comprising using nicotinamide or/and adenine as a substrate, and using a genetically engineered microorganism strain to produce the NAD+, wherein encoding genes of an adenine deaminase in a genome of the genetically engineered microorganism strain are double knocked out, and encoding genes of enzymes in a NAD+ synthesis process are incorporated and overexpressed in the genome of the genetically engineered microorganism strain, wherein the enzymes in the NAD+ synthesis process are Nicotinate phosphoribosyl transferase NPT1 and Nicotinic acid mononucleotide adenylyl transferase NMA1, the strain is diploid Saccharomyces cerevisiae, and the encoding genes of the adenine deaminase are two AAH1 alleles in the diploid Saccharomyces cerevisiae.

2. The method for producing the NAD+ of claim 1, wherein the genetically engineered microorganism whose deposit number is CGMCC No. 19048.

3. The method for producing the NAD+ of claim 1, wherein the method comprises constructing the genetically engineered strain, comprising constructing an expression cassette of the encoding genes of the enzyme in NAD+ synthesis process respectively, and integrating and overexpressing the expression cassette into the genome of a host strain, wherein the encoding genes of the adenine deaminase in the genome have been double knocked out.

4. The method for producing the NAD+ of claim 3, wherein the integrating is through a δ-site integration method.

5. The method for producing the NAD+ of claim 4, wherein the δ-site integration method is a way of gene integration based on a homology of δ sequence, the δ sequence comprises a δ1 fragment and a δ2 fragment, and a first nucleotide sequence of the δ1 fragment is shown in SEQ ID No. 1, and a second nucleotide sequence of the δ2 fragment is shown in SEQ ID No. 2.

* * * * *

SEQUENCE LISTING

```
<160> NUMBER OF SEQ ID NOS: 4

<210> SEQ ID NO 1
<211> LENGTH: 154
<212> TYPE: DNA
<213> ORGANISM: Artificial Sequence
<220> FEATURE:
<223> OTHER INFORMATION: other information:Saccharomyces cerevisiae

<400> SEQUENCE: 1
tgttggaata gaaatcaact atcatctact aactagtatt tacattacta gtatattatc     60
atatacggtg ttagaagatg acgcaaatga tgagaaatag tcatctaaat tagtggaagc    120
tgaaacgcaa ggattgataa tgtaatagga tcaa                                154

<210> SEQ ID NO 2
<211> LENGTH: 180
<212> TYPE: DNA
<213> ORGANISM: Artificial Sequence
<220> FEATURE:
<223> OTHER INFORMATION: other information:Saccharomyces cerevisiae

<400> SEQUENCE: 2
tgaatataaa catataaaat gatgataata atatttatag aattgtgtag aattgcagat     60 tccctttat ggattcctaa atccttgagg agaacttcta gtatattctg tatacctaat    120
attatagcct ttatcaacaa tggaatccca acaattatct caacattcac atatttctca   180

<210> SEQ ID NO 3
<211> LENGTH: 7279
<212> TYPE: DNA
<213> ORGANISM: Artificial Sequence
<220> FEATURE:
<223> OTHER INFORMATION: other information:Recombinant Plasmid

<400> SEQUENCE: 3
ccggtcacac accatagctt caaaatgttt ctactccttt tttactcttc cagattttct     60
cggactccgc gcatcgccgt accacttcaa aacacccaag cacagcatac taaattcccc    120
ctctttcttc ctctagggtg tcgttaatta cccgtactaa aggtttggaa aagaaaaaag    180
agaccgcctc gtttcttttt cttcgtcgaa aaaggcaata aaaattttta tcacgtttct    240 tttcttgaa aatttttttt tttgattttt ttctctttcg atgacctccc attgatattt    300
aagttattaa atggtcttca atttctcaag tttcagtttc atttttcttg ttctattaca    360
acttttttta cttcttgctc attagaaaga aagcatagca atctaatcta agttttaatt    420
acaaagcttg gtaccgagct cggatccact agtaacggcc gccagtgtgc tggaattctg    480
cagatatcca tcacactggc ggccgctcga gcatgcatct agagggccgc atcatgtaat    540
tagttatgtc acgcttacat tcacgccctc cccccacatc cgctctaacc gaaaggaag    600 gagttagaca acctgaagtc taggtcccta tttatttttt tatagttatg ttagtattaa    660
```

```
gaacgttatt tatatttcaa attttctttt tttttctgta cagacgcgtg tacgcatgta      720
acattatact gaaaaccttg cttgagaagg ttttgggacg ctcgaaggct ttaatttgcg      780
gccctgcatt aatgaatcgg ccaacgcgcg gggagaggcg gtttgcgtat tgggcgctct      840
tccgcttcct cgctcactga ctcgctgcgc tcggtcgttc ggctgcggcg agcggtatca      900
gctcactcaa aggcggtaat acggttatcc acagaatcag gggataacgc aggaaagaac      960
atgtgagcaa aaggccagca aaagcccagg aaccgtaaaa aggccgcgtt gctggcgttt     1020
ttccataggc tccgcccccc tgacgagcat cacaaaaatc gacgctcaag tcagaggtgg     1080
cgaaacccga caggactata agataccagg cgtttccccc tggaagctc cctcgtgcgc      1140 tctcctgttc cgaccctgcc gcttaccgga tacctgtccg cctttctccc ttcgggaagc     1200
gtggcgcttt ctcatagctc acgctgtagg tatctcagtt cggtgtaggt cgttcgctcc     1260
aagctgggct gtgtgcacga accccccgtt cagcccgacc gctgcgcctt atccggtaac     1320
tatcgtcttg agtccaaccc ggtaagacac gacttatcgc cactggcagc agccactggt     1380
aacaggatta gcagagcgag gtatgtaggc ggtgctacag agttcttgaa gtggtggcct     1440
aactacggct acactagaag gacagtattt ggtatctgcg ctctgctgaa gccagttacc     1500
ttcggaaaaa gagttggtag ctcttgatcc ggcaaacaaa ccaccgctgg tagcggtggt     1560
ttttttgttt gcaagcagca gattacgcgc agaaaaaaag gatctcaaga agatcctttg     1620
atcttttcta cggggtctga cgctcagtgg aacgaaaact cacgttaagg gattttggtc     1680
atgagattat caaaaaggat cttcacctag atccttttaa attaaaaatg aagttttaaa     1740
tcaatctaaa gtatatatga gtaaacttgg tctgacagtt accaatgctt aatcagtgag     1800
gcacctatct cagcgatctg tctatttcgt tcatccatag ttgcctgact ccccgtcgtg     1860
tagataacta cgatacggga gcgcttacca tctggcccca gtgctgcaat gataccgcga     1920
gacccacgct caccggctcc agatttatca gcaataaacc agccagcgg aagggccgag      1980 cgcagaagtg gtcctgcaac tttatccgcc tccattcagt ctattaattg ttgccgggaa     2040
gctagagtaa gtagttcgcc agttaatagt ttgcgcaacg ttgttggcat tgctacaggc     2100
atcgtggtgt cactctcgtc gtttggtatg gcttcattca gctccggttc caacgatca      2160 aggcgagtta catgatcccc catgttgtgc aaaaaagcgg ttagctcctt cggtcctccg     2220
atcgttgtca gaagtaagtt ggccgcagtg ttatcactca tggttatggc agcactgcat     2280
aattctctta ctgtcatgcc atccgtaaga tgcttttctg tgactggtga gtactcaacc     2340
aagtcattct gagaatagtg tatgcggcga ccgagttgct cttgcccggc gtcaatacgg     2400
gataatagtg tatcacatag cagaacttta aaagtgctca tcattggaaa acgttcttcg     2460
gggcgaaaac tctcaaggat cttaccgctg ttgagatcca gttcgatgta acccactcgt     2520
gcacccaact gatcttcagc atcttttact ttcaccagcg tttctgggtg agcaaaaaca     2580
ggaaggcaaa atgccgcaaa aaagggaata agggcgacac ggaaatgttg aatactcata     2640
ctcttccttt ttcaatgggt aataactgat ataattaaat tgaagctcta atttgtgagt     2700
ttagtataca tgcatttact tataatacag ttttttagtt ttgctgatta agggttctcg     2760
agagctcgtt ttcgacactg gatggcggcg ttagtatcga atcgacagca gtatagcgac     2820
cagcattcac atacgattga cgcatgatat tactttctgc gcacttaact tcgcatctgg     2880
gcagatgatg tcgaggcgaa aaaaaatata aatcacgcta catttgatt aaaatagaac      2940 aactacaata taaaaaaact atacaaatga caagttcttg aaaacaagaa tcttttatt      3000
```

```
gtcagtactg attagaaaaa ctcatcgagc atcaaatgaa actgcaattt attcatatca    3060
ggattatcaa taccatattt ttgaaaaagc cgtttctgta atgaaggaga aaactcaccg    3120
aggcagttcc ataggatggc aagatcctgg tatcggtctg cgattccgac tcgtccaaca    3180
tcaatacaac ctattaattt cccctcgtca aaaataaggt tatcaagtga aaatcacca    3240 tgagtgacga ctgaatccgg tgagaatggc aaaagcttat gcatttcttt ccagacttgt    3300
tcaacaggcc agccattacg ctcgtcatca aaatcactcg catcaaccaa accgttattc    3360
attcgtgatt gcgcctgagc gagacgaaat acgcgatcgc tgttaaaagg acaattacaa    3420
acaggaatcg aatgcaaccg gcgcaggaac actgccagcg catcaacaat attttcacct    3480
gaatcaggat attcttctaa tacctggaat gctgttttgc cggggatcgc agtggtgagt    3540
aaccatgcat catcaggagt acggataaaa tgcttgatgg tcggaagagg cataaattcc    3600
gtcagccagt ttagtctgac catctcatct gtaacatcat tggcaacgct accttttgcca   3660 tgtttcagaa acaactctgg cgcatcgggc ttcccataca atcgatagat tgtcgcacct    3720
gattgcccga cattatcgcg agcccattta tacccatata aatcagcatc catgttggaa    3780
tttaatcgcg gcctcgaaac gtgagtcttt tccttaccca tggttgttta tgttcggatg    3840
tgatgtgaga actgtatcct agcaagattt taaaaggaag tatatgaaag aagaacctca    3900
gtggcaaatc ctaaccttttt atatttctct acagggcgc ggcgtgggga caattcaacg     3960
cgtctgtgag gggagcgttt ccctgctcgc aggtctgcag cgaggagccg taattttgc     4020 ttcgcgccgt gcggccatca aaatgtatgg atgcaaatga ttatacatgg ggatgtatgg    4080
gctaaatgta cgggcgacag tcacatcatg cccctgagct gcgcacgtca agactgtcaa    4140
ggagggtatt ctgggcctcc atgtcgctgg ccgggtgacc cggcggggac gaggcaagct    4200
aaacagatct ctagacctag aattgaattg aaaagctagc ttatcgatga taagctgtca    4260
aagatgagaa ttaattccac ggactataga ctatactaga tactccgtct actgtacgat    4320
acacttccgc tcaggtcctt gtcctttaac gaggccttac cactcttttg ttactctatt    4380
gatccagctc agcaaaggca gtgtgatcta agattctatc ttcgcgatgt agtaaaacta    4440
gctagaccga gaaagagact agaaatgcaa aaggcacttc tacaatggct gccatcatta    4500
ttatccgatg tgacgctgca gcttctcaat gatattcgaa tacgctttga ggagatacag    4560
cctaatatcc gacaaactgt tttacagatt tacgatcgta cttgttaccc atcattgaat    4620
tttgaacatc cgaacctggg agttttccct gaaacagata gtatatttga acctgtataa    4680
taatatatag tctagcgctt tacggaagac aatgtatgta tttcggttcc tggagaaact    4740
attgcatcta ttgcataggt aatcttgcac gtcgcatccc cggttcattt tctgcgtttc    4800
catcttgcac ttcaatagca tatctttgtt aacgaagcat ctgtgcttca ttttgtagaa    4860
caaaaatgca acgcgagagc gctaattttt caaacaaaga atctgagctg cattttttaca   4920 gaacagaaat gcaacgcgaa agcgctattt taccaacgaa gaatctgtgc ttcattttttg   4980 taaaacaaaa atgcaacgcg acgagagcgc taattttttca aacaaagaat ctgagctgca   5040
tttttacaga acagaaatgc aacgcgagag cgctatttta ccaacaaaga atctatactt    5100
cttttttgtt ctacaaaaat gcatcccgag agcgctattt tctaacaaa gcatcttaga    5160 ttactttttt tctccttttgt gcgctctata atgcagtctc ttgataactt tttgcactgt    5220
aggtccgtta aggttagaag aaggctactt tggtgtctat tttctcttcc ataaaaaaag    5280
cctgactcca cttcccgcgt ttactgatta ctagcgaagc tgcgggtgca ttttttcaag    5340
ataaaggcat ccccgattat attctatacc gatgtggatt gcgcatactt tgtgaacaga    5400
```

```
aagtgatagc gttgatgatt cttcattggt cagaaaatta tgaacggttt cttctatttt    5460
gtctctatat actacgtata ggaaatgttt acattttcgt attgttttcg attcactcta    5520
tgaatagttc ttactacaat ttttttgtct aaagagtaat actagagata aacataaaaa    5580
atgtagaggt cgagtttaga tgcaagttca aggagcgaaa ggtggatggg taggttatat    5640
agggatatag cacagagata tatagcaaag agatactttt gagcaatgtt tgtggaagcg    5700
gtattcgcaa tgggaagctc cacccccggtt gataatcaga aaagcccaa aaacaggaag    5760 attgtataag caaatattta aattgtaaac gttaatattt tgttaaaatt cgcgttaaat    5820
ttttgttaaa tcagctcatt ttttaacgaa tagcccgaaa tcgcaaaat cccttataaa    5880 tcaaaagaat agaccgagat agggttgagt gttgttccag tttggaacaa gagtccacta    5940
ttaaagaacg tggactccaa cgtcaaaggg cgaaaaaccg tctatcaggg cgatggccca    6000
ctacgtgaac catcacccta atcaagttttt ttggggtcga ggtgccgtaa agcactaaat    6060
cggaacccta aagggagccc ccgatttaga gcttgacggg gaaagccggc gaacgtggcg    6120
agaaaggaag ggaagaaagc gaaaggagcg ggcgctaggg cgctggcaag tgtagcggtc    6180
acgctgcgcg taaccaccac acccgccgcg cttaatgcgc cgctacaggg cgcgtgggga    6240
tcgatccact agtccacgga ttagaagccg ccgagcgggt gacagccctc cgaaggaaga    6300
ctctcctccg tcgtcctcg tcttcaccgg gttagcatat ctacaattgg gtgaaatggg    6360
gagcgatttg caggcatttg ctcggcatgc cggtagaggt gtggtcaata agagcgacct    6420
catgctatac ctgagaaagc aacctgacct acaggaaaga gttactcaag aataagaatt    6480
ttcgttttaa aacctaagag tcactttaaa atttgtatac acttattttt tttataactt    6540
atttaataat aaaaatcata aatcataaga aattcgcccc gggtcgacag atctttgttt    6600
gtttatgtgt gtttattcga aactaagttc ttggtgtttt aaaactaaaa aaaagactaa    6660
ctataaaagt agaatttaag aagtttaaga aatagattta cagaattaca atcaatacct    6720
accgtcttta tatacttatt agtcaagtag gggaataatt tcagggaact ggtttcaacc    6780 tttttttca gctttttttca aatcagagag agcagaaggt aatagaaggt gtaagaaaat    6840
gagatagata catgcgtggg tcaattgcct tgtgtcatca tttactccag gcaggttgca    6900
tcactccatt gaggttgtgc ccgttttttg cctgtttgtg cccctgttct ctgtagttgc    6960
gctaagagaa tggacctatg aactgatggt tggtgaagaa aacaatattt tggtgctggg    7020 attcttttttt tttctggatg ccagcttaaa aagcgggctc cattatattt agtggatgcc    7080 aggaatattaaac tgttcaccca gacacctacg atgttatata ttctgtgtaa cccgcccccct    7140 attttgggca tgtacggggtt acagcagaat taaaaggcta attttttgac taaataaagt    7200
taggaaaatc actactatta attatttacg tattctttga aatggcagta ttgataatga    7260
taaactcgaa ctgaccggt                                                 7279
```

<210> SEQ ID NO 4
<211> LENGTH: 8883
<212> TYPE: DNA
<213> ORGANISM: Artificial Sequence
<220> FEATURE:
<223> OTHER INFORMATION: other information:Recombinant Plasmid

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

-continued

```
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gacgcgtatt gggatggaac    420
gcggccgcgt ttaaactgtt ggaatagaaa tcaactatca tctactaact agtatttaca    480
ttactagtat attatcatat acggtgttag aagatgacgc aaatgatgag aaatagtcat    540
ctaaattagt ggaagctgaa acgcaaggat tgataatgta ataggatcaa cctgcaggtt    600
aattaactgc aggtcgacaa cccttaatat aacttcgtat aatgtatgct atacgaagtt    660
attaggtcta gagatctgtt tagcttgcct cgtccccgcc gggtcacccg ccagcgaca    720 tggaggccca gaatacccctc cttgacagtc ttgacgtgcg cagctcaggg gcatgatgtg    780
actgtcgccc gtacatttag cccatacatc cccatgtata atcatttgca tccatacatt    840
ttgatggccg cacggcgcga agcaaaaatt acggctcctc gctgcagacc tgcgagcagg    900
gaaacgctcc cctcacagac gcgttgaatt gtccccacgc cgcgcccctg tagagaaata    960
taaaaggtta ggatttgcca ctgaggttct tctttcatat acttcctttt aaaatcttgc   1020
taggatacag ttctcacatc acatccgaac ataaacaacc atgggtaagg aaaagactca   1080
cgtttcgagg ccgcgattaa attccaacat ggatgctgat ttatatgggt ataaatgggc   1140
tcgcgataat gtcgggcaat caggtgcgac aatctatcga ttgtatggga agcccgatgc   1200
gccagagttg tttctgaaac atggcaaagg tagcgttgcc aatgatgtta cagatgagat   1260
ggtcagacta aactggctga cggaatttat gcctcttccg accatcaagc attttatccg   1320
tactcctgat gatgcatggt tactcaccac tgcgatcccc ggcaaaacag cattccaggt   1380
attagaagaa tatcctgatt caggtgaaaa tattgttgat gcgctggcag tgttcctgcg   1440
ccggttgcat tcgattcctg tttgtaattg tccttttaac agcgatcgcg tatttcgtct   1500
cgctcaggcg caatcacgaa tgaataacgg tttggttgat gcgagtgatt ttgatgacga   1560
gcgtaatggc tggcctgttg aacaagtctg gaaagaaatg cataagcttt tgccattctc   1620
accggattca gtcgtcactc atggtgattt ctcacttgat aaccttattt ttgacgaggg   1680
gaaattaata ggttgtattg atgttggacg agtcggaatc gcagaccgat accaggatct   1740
tgccatccta tggaactgcc tcggtgagtt ttctccttca ttacagaaac ggctttttca   1800
aaaatatggt attgataatc ctgatatgaa taaattgcag tttcatttga tgctcgatga   1860 gttttttctaa tcagtactga caataaaaag attcttgttt tcaagaactt gtcatttgta   1920
tagttttttt atattgtagt tgttctattt taatcaaatg ttagcgtgat ttatattttt   1980
tttcgcctcg acatcatctg cccagatgcg aagttaagtg cgcagaaagt aatatcatgc   2040
gtcaatcgta tgtgaatgct ggtcgctata ctgctgtcga ttcgatacta acgccgccat   2100
ccagtgtcga aaacgagctc tcgagaaccc ttaatataac ttcgtataat gtatgctata   2160
cgaagttatt aggtgatatc agatccacta gtgatttaaa ttgcaggccc gttagcatat   2220
ctacaattgg gtgaaatggg gagcgatttg caggcatttg ctcggcatgc cggtagaggt   2280
gtggtcaata agagcgacct catgctatac ctgagaaagc aacctgacct acaggaaaga   2340
gttactcaag aataagaatt ttcgttttaa aacctaagag tcactttaaa atttgtatac   2400
acttattttt tttataactt atttaataat aaaaatcata aatcataaga aattcgcccc   2460
gggttcattc tttgtttcca agaacttgct taacaggttc ggtttggtcc acatatagtc   2520
```

```
tatgttcttg gatatacctg atgaccgaat taggtaacaa atattgtaca gacatggcgc    2580
gtctgataaa tagacgaact ttcgtggaag aaatatcatt atagatgagt tgcttgatga    2640
taagaatatt ccttctatgt tcatacataa tatcatggga taacaaaaaa gaccttacat    2700
cagaaccagt acgttcgaca atcaaacaac cgtaattacc gagaatgtga tgtaaatcgg    2760
cgtccgccca aacgtttggt tcacccattg actctattag gtcaccacca gccagcaaca    2820
ttattttcac accaattttt tctccagtaa cagtagctac accacctctc ttaatattga    2880
tttcgtgatt gaaatgatcc aagaccttgg cagttcttgt gtatgaaggt tgcaatgact    2940
cccatgcatc caccatcaac caagatgagg ttctttcgca ggccaattca cacatacgta    3000
ctctatggta ggatggggcc aagccttgct tttgatagtt atcactaaca ggggagtaat    3060
atccacctat gacttcaaac cttgtttgtt cagagattgc atctaaagcc atttcaaaca    3120
ttcttagatg caagtaggtg attggtgaaa agacccaca tgctactatt actaacggca     3180
gtttatttgg atccagtaat ttttcgata atctgtgtga ggggaattcg tagtcttcca     3240
aggttcttgc ttgacgaacg attccatgtg gaacttcttc taaatcagca atctgatatt    3300
tctgaacacc tctagtttct gattctgtgg ttgaatctga accgtatctc tccttggatc    3360
taaaatccgc gtcatcatct tcggaagaca cttctgcgga aagtggttga aagtcgtctt    3420
ggttcaatgg aatatgctga tgttttttat cattgccttc tttacgactg tgatgatggt    3480
gatgatgatg cttaggatgc ttttttcttcc tcttaatatt aaaaggtgca tctatagagg    3540
aattcgcatc ggctaagacg tatgaataa ttggaataga tttgggaatt ttagattccg      3600
ggtcgggtgg aggaatcaat tcctcgtctg cagatggcgg tttgaaatcc ggagctcttg    3660
tgggatccat tttgtttgtt tatgtgtgtt tattcgaaac taagttcttg gtgttttaaa    3720
actaaaaaaa agactaacta taaaagtaga atttaagaag tttaagaaat agatttacag    3780
aattacaatc aatacctacc gtctttatat acttattagt caagtagggg aataatttca    3840
gggaactggt ttcaaccttt tttttcagct tttttcaaat cagagagagc agaaggtaat    3900
agaaggtgta agaaaatgag atagatacat gcgtgggtca attgccttgt gtcatcattt    3960
actccaggca ggttgcatca ctccattgag gttgtgcccg ttttttgcct gtttgtgccc    4020
ctgttctctg tagttgcgct aagagaatgg acctatgaac tgatggttgg tgaagaaaac    4080
aatattttgg tgctgggatt cttttttttt ctggatgcca gcttaaaaag cgggctccat    4140
tatatttagt ggatgccagg aataaactgt tcacccagac acctacgatg ttatatattc    4200
tgtgtaaccc gcccctatt tgggcatgt acgggttaca gcagaattaa aaggctaatt       4260
ttttgactaa ataaagttag gaaaatcact actattaatt atttacgtat tctttgaaat    4320
ggcagtattg ataatgataa actcgaactg accggtccgg tcacacacca tagcttcaaa    4380
atgtttctac tccttttta ctcttccaga ttttctcgga ctccgcgcat cgccgtacca     4440
cttcaaaaca cccaagcaca gcatactaaa ttcccctct ttcttcctct agggtgtcgt     4500
taattacccg tactaaaggt ttggaaaaga aaaagagac cgcctcgttt cttttcttc      4560 gtcgaaaaag gcaataaaaa tttttatcac gtttctttt cttgaaaatt ttttttttg      4620 attttttct ctttcgatga cctcccattg atatttaagt tattaaatgg tcttcaattt     4680
ctcaagtttc agtttcattt ttcttgttct attacaactt ttttacttc ttgctcatta     4740 gaaagaaagc atagcaatct aatctaagtt ttaattacaa aggatccatg tcagaaccag    4800
tgataaagtc tcttttggac acagacatgt acaagattac gatgcatgct gctgtcttca    4860
```

```
ctaattttcc agatgttaca gttacttata aatataccaa caggtcgtcc caattgacct    4920
tcaataagga agccattaat tggttgaaag agcaattttc gtatttggga aatttgaggt    4980
tcacagaaga ggaaattgaa tacttaaaac aggaaatccc atatttgcca tcggcatata    5040
ttaagtatat tagcagttct aattacaaac tacaccctga agagcagatt tccttcactt    5100
cagaagaaat cgagggcaag cccacccact acaaattgaa aattttagtc agtggtagtt    5160
ggaaggatac tatcctttat gagatcccct tactgtccct aatatcagaa gcgtatttta    5220
aatttgttga catcgactgg gactacgaaa accaattaga acaagctgag aagaaggcgg    5280
aaactttgtt tgataatggt attagattca gtgaatttgg tacaagacgt cgtagatctc    5340
tgaaggctca agatctaatt atgcaaggaa tcatgaaagc tgtgaacggt aacccagaca    5400
gaaacaaatc gctattatta ggcacatcaa atattttatt tgccaagaaa tatggagtca    5460
agccaatcgg tactgtggct cacgagtggg ttatgggagt cgcttctatt agtgaagatt    5520
atttgcatgc caataaaaat gcaatggatt gttggatcaa tacttttggt gcaaaaaatg    5580
ctggtttagc attaacggat acttttggaa ctgatgactt tttaaaatca ttccgtccac    5640
catattctga tgcttacgtc ggtgttagac aagattctgg agacccagtt gagtatacca    5700
aaaagatttc ccaccattac catgacgtgt tgaaattgcc taaattctcg aagattatct    5760
gttattccga ttctttgaac gtcgaaaagg caataactta ctcccatgca gctaaagaga    5820
atggaatgct agccacattc ggtattggca caaactttac taatgatttt cgtaagaagt    5880
cagaacccca ggttaaaagt gagccgttaa acatcgttat caaactatta gaagtaaatg    5940
gtaatcacgc tatcaaaatt tctgataact taggtaaaaa tatgggagat cctgccactg    6000
tgaagagagt gaaagaggaa ttgggatata ctgaacgaag ttggagtggt gataacgaag    6060
cgcacagatg gacctaagaa ttctgcagat atccatcaca ctggcggccg ctcgagcatg    6120
catctagagg gccgcatcat gtaattagtt atgtcacgct tacattcacg ccctcccccc    6180
acatccgctc taaccgaaaa ggaaggagtt agacaacctg aagtctaggt ccctatttat    6240 tttttatag ttatgttagt attaagaacg ttatttatat ttcaaatttt tcttttttt    6300 ctgtacagac gcgtgtacgc atgtaacatt atactgaaaa ccttgcttga aaggttttg    6360 ggacgctcga aggctttaat ttgcaagctg cggccctgca ttaatgaatc ggccaaccca    6420
tgcgggtgaa ataaacata taaaatgatg ataataatat ttatagaatt gtgtagaatt    6480
gcagattccc ttttatggat tcctaaatcc ttgaggagaa cttctagtat attctgtata    6540
cctaatatta tagcctttat caacaatgga atcccaacaa ttatctcaac attcacatat    6600
ttctcagttt aaacgcggcc gcgttccatc ccaatggcgc gccgagcttg gcgtaatcat    6660
ggtcatagct gtttcctgtg tgaaattgtt atccgctcac aattccacac aacatacgag    6720
ccggaagcat aaagtgtaaa gcctggggtg cctaatgagt gagctaactc acattaattg    6780
cgttgcgctc actgcccgct ttccagtcgg gaaacctgtc gtgccagctg cattaatgaa    6840
tcggccaacg cgcggggaga ggcggtttgc gtattgggcg ctcttccgct tcctcgctca    6900
ctgactcgct gcgctcggtc gttcggctgc ggcgagcggt atcagctcac tcaaaggcgg    6960
taatacggtt atccacagaa tcaggggata acgcaggaaa gaacatgtga gcaaaaggcc    7020
agcaaaaggc caggaaccgt aaaaaggccg cgttgctggc gttttccat aggctccgcc    7080 cccctgacga gcatcacaaa aatcgacgct caagtcagag gtggcgaaac ccgacaggac    7140
tataaagata ccaggcgttt ccccctggaa gctccctcgt gcgctctcct gttccgaccc    7200
tgccgcttac cggatacctg tccgcctttc tcccttcggg aagcgtggcg ctttctcata    7260
```

```
gctcacgctg taggtatctc agttcggtgt aggtcgttcg ctccaagctg ggctgtgtgc    7320 acgaacccc cgttcagccc gaccgctgcg ccttatccgg taactatcgt cttgagtcca     7380
acccggtaag acacgactta tcgccactgg cagcagccac tggtaacagg attagcagag    7440
cgaggtatgt aggcggtgct acagagttct tgaagtggtg gcctaactac ggctacacta    7500
gaagaacagt atttggtatc tgcgctctgc tgaagccagt taccttcgga aaaagagttg    7560
gtagctcttg atccggcaaa caaccaccg ctggtagcgg tggttttttt gtttgcaagc     7620
agcagattac gcgcagaaaa aaaggatctc aagaagatcc tttgatcttt tctacggggt    7680
ctgacgctca gtggaacgaa aactcacgtt aagggatttt ggtcatgaga ttatcaaaaa    7740
ggatcttcac ctagatcctt ttaaattaaa aatgaagttt taaatcaatc taaagtatat    7800
atgagtaaac ttggtctgac agttaccaat gcttaatcag tgaggcacct atctcagcga    7860
tctgtctatt tcgttcatcc atagttgcct gactccccgt cgtgtagata actacgatac    7920
gggagggctt accatctggc cccagtgctg caatgatacc gcgagaccca cgctcaccgg    7980
ctccagattt atcagcaata accagccag ccggaagggc cgagcgcaga agtggtcctg     8040
caactttatc cgcctccatc cagtctatta attgttgccg ggaagctaga gtaagtagtt    8100
cgccagttaa tagtttgcgc aacgttgttg ccattgctac aggcatcgtg gtgtcacgct    8160
cgtcgtttgg tatggcttca ttcagctccg gttcccaacg atcaaggcga gttacatgat    8220
cccccatgtt gtgcaaaaaa gcggttagct ccttcggtcc tccgatcgtt gtcagaagta    8280
agttggccgc agtgttatca ctcatggtta tggcagcact gcataattct cttactgtca    8340
tgccatccgt aagatgcttt tctgtgactg gtgagtactc aaccaagtca ttctgagaat    8400
agtgtatgcg gcgaccgagt tgctcttgcc cggcgtcaat acgggataat accgcgccac    8460
atagcagaac tttaaaagtg ctcatcattg gaaaacgttc ttcggggcga aaactctcaa    8520
ggatcttacc gctgttgaga tccagttcga tgtaacccac tcgtgcaccc aactgatctt    8580
cagcatcttt tactttcacc agcgtttctg ggtgagcaaa aacaggaagg caaaatgccg    8640
caaaaaaggg aataagggcg acacggaaat gttgaatact catactcttc ctttttcaat    8700
attattgaag catttatcag ggttattgtc tcatgagcgg atacatattt gaatgtattt    8760
agaaaaataa acaaataggg gttccgcgca catttccccg aaaagtgcca cctgacgtct    8820
aagaaaccat tattatcatg acattaacct ataaaaatag gcgtatcacg aggccctttc    8880
gtc                                                                  8883
```